United States Patent
Kydonieus et al.

(10) Patent No.: US 9,895,384 B1
(45) Date of Patent: Feb. 20, 2018

(54) ABUSE DETERRENT OPIOID AGONIST TRANSDERMAL COMPOSITIONS AND METHODS FOR THEIR USE

(71) Applicant: InteguRx Therapeutics, LLC, Califon, NJ (US)

(72) Inventors: Agis Kydonieus, Kendall Park, NJ (US); Spencer Knapp, Skillman, NJ (US)

(73) Assignee: InteguRx Therapeutics, LLC, Califon, NJ (US)

( * ) Notice: Subject to any disclaimer, the term of this patent is extended or adjusted under 35 U.S.C. 154(b) by 0 days.

(21) Appl. No.: 15/088,417

(22) Filed: Apr. 1, 2016

Related U.S. Application Data

(60) Provisional application No. 62/142,633, filed on Apr. 3, 2015.

(51) Int. Cl.
| | |
|---|---|
| *A61K 31/695* | (2006.01) |
| *A61K 9/00* | (2006.01) |
| *A61K 31/485* | (2006.01) |
| *A61K 47/12* | (2006.01) |
| *A61K 9/06* | (2006.01) |
| *A61K 47/32* | (2006.01) |

(52) U.S. Cl.
CPC .......... *A61K 31/695* (2013.01); *A61K 9/0014* (2013.01); *A61K 9/06* (2013.01); *A61K 31/485* (2013.01); *A61K 47/12* (2013.01); *A61K 47/32* (2013.01)

(58) Field of Classification Search
None
See application file for complete search history.

(56) References Cited

U.S. PATENT DOCUMENTS 8,309,568 B2 * 11/2012 Stinchcomb ......... A61K 31/439
514/279
2006/0063792 A1 3/2006 Dolle et al.

FOREIGN PATENT DOCUMENTS

WO WO 2011/133346 4/2010

OTHER PUBLICATIONS

Nagase et al. "The Facility of Formation of Bond in Dihydromorphinone and Related Opiates", Department of Medicinal Chemistry, College of Pharmacy, University of Minnesota, Journal of Organic Chemistry, vol. 54, No. 17, pp. 4170-4125, 1989.
Koolpe et al., "Opioid Agonists and Antagonists, 6-Desoxy-6-substituted Lactone, Epoxide, and Glycidate Ester Derivatives of Naltrexone and Oxymorphone", Journal of Medicinal Chemistry, vol. 28, No. 7, pp. 949-957, 1985.
Hammell et al. "A Duplex "Gemini" Prodrug of Naltrexone for Transdermal Delivery", Journal of Controlled Release, vol. 97, pp. 283-290, 2004.

* cited by examiner

*Primary Examiner* — Karl J Puttlitz
(74) *Attorney, Agent, or Firm* — Baker Hostetler LLP

(57) ABSTRACT

The present disclosure is directed to abuse-resistant transdermal delivery compositions comprising opioid agonists.

14 Claims, No Drawings

ABUSE DETERRENT OPIOID AGONIST TRANSDERMAL COMPOSITIONS AND METHODS FOR THEIR USE

CROSS REFERENCE TO RELATED APPLICATIONS

This application claims the benefit of U.S. Provisional Application No. 62/142,633, filed Apr. 3, 2015, the entirety of which is incorporated herein by reference.

TECHNICAL FIELD

The present disclosure is directed to abuse-resistant transdermal delivery compositions comprising opioid agonists.

BACKGROUND

Prescription opioids are part of the arsenal of analgesic formulations for the management of pain in humans. However, these products are often misused and/or abused, causing major public health care issues. Current opioid formulations are easily manipulated to enable abuse. Therefore, there is a substantial unmet need in the health care field for opioid formulations that deter or prevent misuse and/or abuse.

SUMMARY

The disclosure is directed to transdermal compositions comprising an opioid agonist and at least one opioid antagonist conjugate. These transdermal compositions may optionally include one or more excipients such as transdermal skin enhancers, plasticizers, humectants, antioxidants, or combinations thereof. Methods of using these transdermal compositions are also described.

DETAILED DESCRIPTION OF ILLUSTRATIVE EMBODIMENTS

The present invention may be understood more readily by reference to the following detailed description taken in connection with the accompanying figures and examples that form a part of this disclosure. It is to be understood that this invention is not limited to the specific devices, methods, applications, conditions or parameters described and/or shown herein and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the invention that are, for clarity, described herein in the context of separate embodiments, may also be provided in combination in a single embodiment. Conversely, various features of the invention that are, for brevity, described in the context of a single embodiment, may also be provided separately or in any subcombination. Further, references to values stated in ranges include each and every value within that range. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Finally, while an embodiment may be described as part of a series of steps or part of a more general structure, each said step may also be considered an independent embodiment in itself The present disclosure is directed to transdermal compositions comprising an opioid agonist and at least one opioid antagonist conjugate. These compositions can be provided in any transdermal delivery form known in the art.

In one embodiment of the disclosure, the transdermal compositions of the disclosure are in the form of a transdermal device that is a drug-in-adhesive device. In such embodiments, the adhesive is preferably a pressure-sensitive adhesive. Pressure-sensitive adhesives suitable for use in transdermal delivery systems are known in the art and include, for example, silicone, a polyisobutylene polymer, or an acrylate copolymer, or a combination thereof.

In other embodiments of the disclosure, the transdermal compositions of the disclosure are in the form of transdermal gels. The preparation of transdermal gels is known in the art.

The opioid agonists for use in the disclosure can be any opioid agonist known in the art. Preferred examples of opioid agonists include, but are not limited to, codeine, dihydrocodeine, hydrocodone, hydromorphone, levorphanol, meperidine, fentanyl, fentanyl derivatives, dipipanone, heroin, tramadol, etorphine, dihydroetorphine, methadone, morphine, oxycodone, oxymorphone, propoxyphene, sufentanil, or buprenorphine, pharmaceutically acceptable salts thereof, and combinations thereof.

The transdermal compositions of the disclosure can include up to 40% wt. % of the opioid agonist, by weight of the transdermal composition. Preferably, the transdermal compositions include from about 0.1 wt. % to about 25 wt. % of the opioid agonist, by weight of the transdermal composition. In addition, the transdermal compositions may include from about 0.1 wt. % to about 22 wt. %, 0.1 wt. % to about 20 wt. %, about 0.1 wt. % to about 17 wt. %, about 0.1 wt. % to about 15 wt. %, about 0.1 wt. % to about 12 wt. %, about 0.1 wt. % to about 10 wt. % about 0.1 wt. % to about 7 wt. %, about 0.1 wt. % to about 5 wt. %, about 0.1 wt. % to about 2 wt. %, about 0.1 wt. % to about 1.0 wt. %, about 0.5 wt. % to about 25 wt. %, about 0.5 wt. % to about 22 wt. %, about 0.5 wt. % to about 20 wt. %, about 0.5 wt. % to about 17 wt. %, about 0.5 wt. % to about 15 wt. %, about 0.5 wt. % to about 12 wt. %, about 0.5 wt. % to about 10 wt. %, about 0.5 wt. % to about 7 wt. %, about 0.5 wt. % to about 5 wt. %, about 0.5 wt. % to about 1.0 wt. %, 1.0 wt. % to about 22 wt. %, 1.0 wt. % to about 20 wt. %, about 1.0 wt. % to about 17 wt. %, about 1.0 wt. % to about 15 wt. %, about 1.0 wt. % to about 12 wt. %, about 1.0 wt. % to about 10 wt. % about 1.0 wt. % to about 7 wt. %, about 1.0 wt. % to about 5 wt. %, about 1.0 wt. % to about 2 wt. %, 5.0 wt. % to about 22 wt. %, 5.0 wt. % to about 20 wt. %, about 5.0 wt. % to about 17 wt. %, about 5.0 wt. % to about 15 wt. %, about 5.0 wt. % to about 12 wt. %, about 5.0 wt. % to about 10 wt. % about 5.0 wt. % to about 7 wt. %, 10.0 wt. % to about 22 wt. %, 10.0 wt. % to about 20 wt. %, about 10.0 wt. % to about 17 wt. %, about 10.0 wt. % to about 15 wt. %, about 10.0 wt. % to about 12 wt. %, of the opioid agonist, by weight of the transdermal composition. The transdermal compositions of the disclosure can also include 40 wt. %, 35 wt. %, 30 wt. %, 25 wt. %, 22 wt. %, 20 wt.

%, 17 wt. %, 15 wt. %, 12 wt. %, 10 wt. %, 7 wt. %, 5 wt. %, 2 wt. %, 1 wt. %, 0.9 wt. %, 0.8 wt. %, 0.7 wt. %, 0.6 wt. %, 0.5 wt. %, 0.4 wt. %, 0.3 wt. %, 0.2 wt. %, and 0.1 wt. %, of the opioid agonist, by weight of the transdermal composition. As used herein, "opioid antagonist conjugate" refers to a compound formed by the joining of an opioid antagonist moiety to one or more other opioid antagonist moieties using one or more linkers.. The opioid antagonist moieties included in the opioid antagonist conjugates of the disclosure may be the same or different. The opioid antagonist moieties for use in the disclosure can be derived from any opioid antagonists known in the art. Preferred examples of opioid antagonists include, but are not limited to, naltrexone and naloxone, and pharmaceutically acceptable salts thereof The transdermal compositions of the disclosure can include up to 40% wt. % of the opioid antagonist conjugate, by weight of the transdermal composition. Preferably, the transdermal compositions include about 0.1 wt. % to about 25 wt. % of the opioid antagonist conjugate, by weight of the transdermal composition. In addition, the transdermal compositions may include from about 0.1 wt. % to about 22 wt. %, 0.1 wt. % to about 20 wt. %, about 0.1 wt. % to about 17 wt. %, about 0.1 wt. % to about 15 wt. %, about 0.1 wt. % to about 12 wt. %, about 0.1 wt. % to about 10 wt. %, about 0.1 wt. % to about 7 wt. %, about 0.1 wt. % to about 5 wt. %, about 0.1 wt. % to about 2 wt. %, about 0.1 wt. % to about 1.0 wt. %, about 0.5 wt. % to about 25 wt. %, about 0.5 wt. % to about 22 wt. %, about 0.5 wt. % to about 20 wt. %, about 0.5 wt. % to about 17 wt. %, about 0.5 wt. % to about 15 wt. %, about 0.5 wt. % to about 12 wt. %, about 0.5 wt. % to about 10 wt. %, about 0.5 wt. % to about 7 wt. %, about 0.5 wt. % to about 5 wt. %, about 0.5 wt. % to about 1.0 wt. %, 1.0 wt. % to about 22 wt. %, 1.0 wt. % to about 20 wt. %, about 1.0 wt. % to about 17 wt. %, about 1.0 wt. % to about 15 wt. %, about 1.0 wt. % to about 12 wt. %, about 1.0 wt. % to about 10 wt. % about 1.0 wt. % to about 7 wt. %, about 1.0 wt. % to about 5 wt. %, about 1.0 wt. % to about 2 wt. %, 5.0 wt. % to about 22 wt. %, 5.0 wt. % to about 20 wt. %, about 5.0 wt. % to about 17 wt. %, about 5.0 wt. % to about 15 wt. %, about 5.0 wt. % to about 12 wt. %, about 5.0 wt. % to about 10 wt. % about 5.0 wt. % to about 7 wt. %, 10.0 wt. % to about 22 wt. %, 10.0 wt. % to about 20 wt. %, about 10.0 wt. % to about 17 wt. %, about 10.0 wt. % to about 15 wt. %, about 10.0 wt. % to about 12 wt. %, of the opioid antagonist conjugate, by weight of the transdermal composition. The transdermal compositions of the disclosure can also include 40 wt. %, 35 wt. %, 30 wt. %, 25 wt. %, 22 wt. %, 20 wt. %, 17 wt. %, 15 wt. %, 12 wt. %, 10 wt. %, 7 wt. %, 5 wt. %, 2 wt. %, 1 wt. %, 0.9 wt. %, 0.8 wt. %, 0.7 wt. %, 0.6 wt. %, 0.5 wt. %, 0.4 wt. %, 0.3 wt. %, 0.2 wt. %, and 0.1 wt. %, of the opioid antagonist conjugate, by weight of the transdermal composition.

The opioid antagonist moieties can be joined using linkers to form "dimer" opioid antagonist conjugates. These "dimer" opioid antagonist conjugates include two opioid antagonist moieties joined together through a linker.

The opioid antagonist moieties can also be joined using linkers to form "trimer" opioid antagonist conjugates. These "trimer" opioid antagonist conjugates include three opioid antagonist moieties. Higher order opioid antagonist conjugates including four, five, or six opioid antagonist moieties are also within the scope of the disclosure.

The opioid antagonist conjugates of the disclosure have larger molecular weights, as compared to the molecular weights of the non-conjugated opioid antagonist moieties. Those skilled in the art understand that higher molecular weight compounds do not easily permeate through the skin. The opioid antagonist conjugates for use in the disclosure should be of a molecular weight such that they do not permeate through the skin over the course of a period of time during which the transdermal compositions of the disclosure are in contact with the skin of the patient, for example, 4, 6, 12, 18, 20, 24, 84, or 168 hours. Preferred opioid antagonist conjugates have a molecular weight of at least 500 Daltons, for example 500 to 5000 Daltons, with 500 to 1500 Daltons being particularly preferred. The molecular weights of the opioid antagonist conjugates of the disclosure can be determined using methods known in the art.

The opioid antagonist conjugates described herein have linkers that degrade, thereby releasing the opioid antagonist(s), under conditions not typically associated with prescribed uses for transdermal compositions. That is, the linkers degrade, resulting in release of opioid antagonist, if a patient attempts to abuse the transdermal compositions in order to achieve a euphoric effect from the opioid agonist present in the compositions. The released opioid antagonist will then block any euphoric effect of the opioid agonist. Abuse deterrence can thereby be achieved, by using the compositions of the disclosure.

The linkers may be selected such that an opioid antagonist conjugate has a longer half-life compared to the half-life of the non-conjugated opioid antagonist. A preferred opioid antagonist conjugate would have a half-life at least as long as the opioid agonist that is being administered. For example, naloxone has a very short half-life of between about 30 to about 80 minutes. Naloxone antagonist conjugates may be prepared by selecting a linker such that the half-life of the naloxone antagonist conjugate is about 5 or more days.

The degradation of the linkers may be achieved, for example, via hydrolysis or enzymatic cleavage. The release of the opioid antagonist may occur at a pre-selected pH. In one embodiment, the opioid antagonist conjugates degrade to produce the opioid antagonist at a pH of between 2 and 3. Degradation of the opioid antagonist conjugate at a pH of between 2 and 3 will result in the release the opioid antagonist in the stomach, which may prevent or deter oral consumption of the transdermal compositions of the disclosure.

In another embodiment, the opioid antagonist conjugates degrade to produce the opioid antagonist at a pH of between 6 and 8. Degradation of the opioid antagonist conjugate at a pH of between 6 and 8 will release the opioid antagonist in the blood, which may prevent or deter the snorting or injecting of the transdermal compositions of the disclosure.

The pH of the transdermal compositions of the disclosure may be maintained at levels such that hydrolysis of the opioid antagonist conjugates cannot take place, thereby preventing release of the antagonist within the transdermal compositions themselves, when used as prescribed. Small amounts of an acidifying agent may be incorporated into the transdermal compositions to maintain a low pH level, for example, pH 6 or less. Preferred acidifying agents include, but are not limited to, citric acid, acetic acid, and nitric acid.

Alternatively, small amounts of an alkalinizing agent may be incorporated into the transdermal compositions to maintain higher pH levels, for example, pH 8 or greater. Preferred alkalinizing agents include, but are not limited to, sodium carbonate, ammonium carbonate, sodium borate, potassium hydroxide, diethanolamine, triethanolamine, and specific polymers, such as EUDRAGIT™—acrylate/methacrylate polymers E 100, S 100 and RL 100, that contain quaternary ammonium groups.

Various linkers known in the art may be used to make the opioid antagonist conjugates of the disclosure. Examples of linkers useful in the disclosure include, but are not limited to, silyl linkers, sulfamate linkers, and ester linkers. Some silyl linkers will hydrolyze at a pH of between about 2 and about 3. Other silyl linkers will hydroyze at a pH of about 7.4, depending on the structure and steric hindrance of the opioid antagonist conjugate. Subgroups of silyl linkers are known in the art to have various rates of hydrolysis. The order of hydrolysis of exemplary silyl linker subgroups is as follows: silyl<disiloxane<succinate bis(silyl). In addition, the rate of hydrolysis of silyl linkers can be reduced considerably by changing the silyl substituent from methyl to ethyl, which increases the steric hindrance at silicon.

Sulfamate linkers (—O—SO$_2$—) hydrolyze at a pH-independent rate below pH 7.4, depending on the structure of the conjugate compound.

Ester linkers are fairly stable to chemical hydrolysis, depending on the structure of the conjugate compound, but are susceptible to enzyme-mediated cleavage.

Preferred "dimer" opioid antagonist conjugates of the disclosure include Structures 1 and 2, which include silyl linkers:

Structure 1

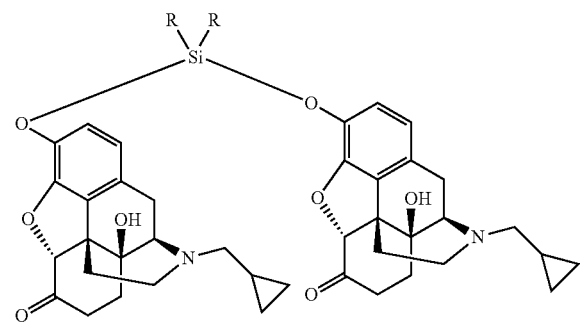

Structure 2

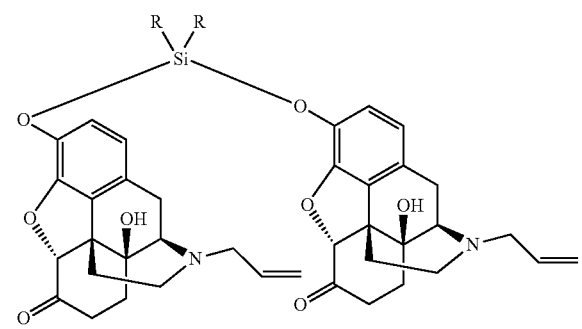

The R groups shown in structure 1 and structure 2 may each independently be C$_{1-6}$ alkyl, for example, methyl, ethyl, propyl, isopropyl, butyl, and the like. The rate of release of the opioid antagonist via degradation of the opioid antagonist conjugate may be modulated by adjusting the size of the R groups.

Other preferred "dimer" opioid antagonist conjugates for use in the disclosure include Structures 3 and 4, which include disiloxane linkers.

Structure 3

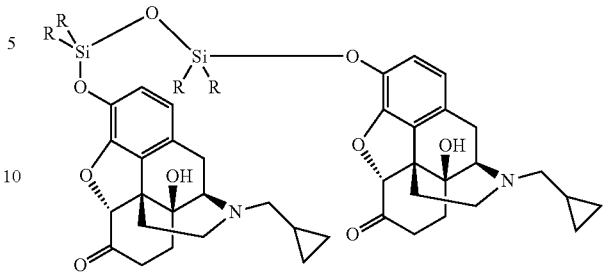

Structure 4

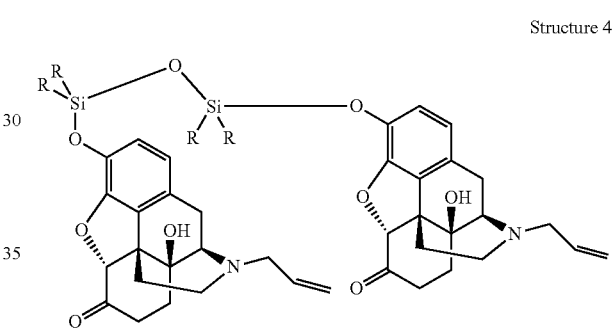

The R groups shown in structure 3 and structure 4 may each independently be C$_{1-6}$ alkyl, for example, methyl, ethyl, propyl, isopropyl, butyl, and the like. The rate of release of the opioid antagonist via degradation of the opioid antagonist conjugate may be modulated by adjusting the size of the R groups.

Other preferred opioid antagonist conjugates that include succinate silyl linkers are Structures 5 and 6. The length, nature, and substitution pattern of the connecting chain may be adjusted according to the properties desired.

Structure 5

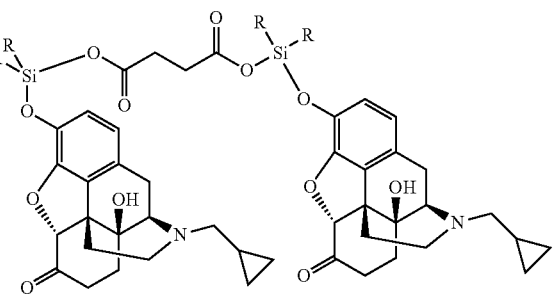

Structure 6

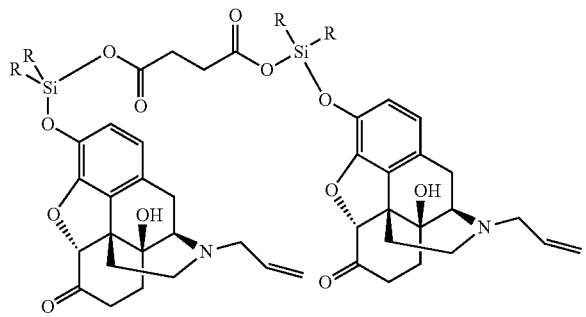

The R groups shown in structure 5 and structure 6 may each independently be $C_{1-6}$ alkyl, for example, methyl, ethyl, propyl, isopropyl, butyl, and the like. The rate of release of the opioid antagonist via degradation of the opioid antagonist conjugate may be modulated by adjusting the size of the R groups.

Diester linkers can also be used in the opioid antagonist conjugate of the disclosure. Preferred diester "dimers" are Structures 7 and 8. The length, nature, and substitution of the connecting chain can be adjusted according to the properties desired.

Structure 7

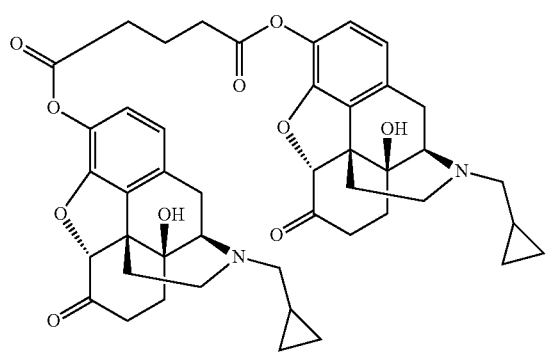

Structure 8

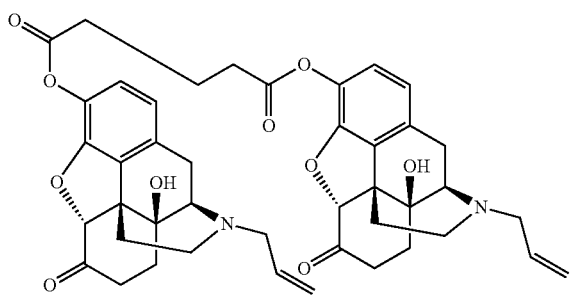

The opioid antagonist conjugates for use in the disclosure may also include a polymeric conjugate, in which the opioid antagonist moiety is attached to a hydroxyl group of a polymer through a linker. For example, the opioid antagonist moiety may be attached to partially deacetylated polyvinyl acetate using a silyl or other linker. These polymeric conjugates may be mixed with acrylic vinyl acetate copolymer pressure-sensitive adhesives, or any other adhesive suitable for use in transdermal delivery. A preferred opioid antagonist conjugate of this type includes Structure 9, wherein each R is independently $C_{1-6}$ alkyl, for example, methyl, ethyl, propyl, isopropyl, butyl, and the like, or analogous aloxy alaogues, for example, methoxy, ethoxy, propoxy, isopropoxy, butoxy, and the like.

Structure 9

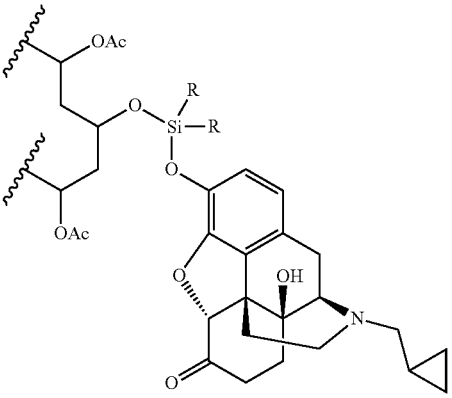

The transdermal compositions of the disclosure can optionally be combined with one or more excipients. The excipients can comprise up to 99 wt. %, based on the weight of the transdermal composition. In addition, the excipients can comprise up to 95, 90, 85, 80, 75, 70, 65, 60, 55, 50, 45, 40, 35, 30, 25, 20, 15, 10, 5, or 1 wt. %, based on the weight of the transdermal composition. Preferred excipients include, for example, transdermal skin enhancers, plasticizers, humectants, antioxidants, and combinations thereof. The addition of such excipients can be used to form the desired transdermal delivery form, for example, a drug-in-adhesive device or gel. Preferred excipients are described in, for example, WO2014/031958, the entirety of which is incorporated by reference herein.

Another component for use in the described transdermal compositions, for use alone or in combination with other excipients, is a pressure sensitive adhesive. The transdermal compositions of the disclosure can comprise 50 wt. % or greater, based on the weight of the adhesive composition, of one or more pressure sensitive adhesives. For example, the transdermal compositions can comprise from about 50 wt. % to about 99 wt. % of a pressure sensitive adhesive. In some embodiments, the transdermal compositions comprise about 50, 55, 60, 65, 70, 75, 80, 85, 90, 95, or 99 wt. % of pressure sensitive adhesive.

In some embodiments, the transdermal compositions of the disclosure can include a transdermal skin enhancer. A preferred transdermal skin enhancer comprises levulinic acid and a straight chain fatty acid with one or more double bonds. Other preferred transdermal skin enhancers are described in WO 2014/031958, the entirety of which is incorporated by reference herein.

In other embodiments, the transdermal compositions of the disclosure can include a plasticizer. Preferred plasticizers include, for example, glycerol, polybutylene, or a combination thereof.

The transdermal compositions of the disclosure can also include a humectant. Preferred humectants include, for example, polyvinyl pyrrolidone or polyvinyl pyrrolidone vinyl acetate copolymer, or a combination thereof.

In yet other embodiments, the transdermal compositions of the disclosure can include an antioxidant. Preferred antioxidants include, for example, butylated hydroxytoluene, butylated hydroxyanisole, propyl gallate, sodium metabisulfite, or tocopherol, or a combination thereof.

The transdermal compositions of the disclosure can be used for treating any condition known to be treated using opioid agonists. Preferably, the transdermal compositions of the disclosure are using to treat pain in a patient.

In a preferred embodiment, the transdermal compositions are in the form of a transdermal patch. Methods for producing transdermal patches are described herein and are known in the art. The patch is applied to the skin of the patient in order to treat the condition.

In another embodiment, the transdermal compositions are in the form of a gel. Methods for producing transdermal gels are known in the art. The gel is applied to the skin of the patient in order to treat the condition.

While the foregoing description and examples are illustrative of preferred embodiments of the disclosure, it will be noted that various changes and modifications can be made without departing from the spirit and scope of the inventions.

EXAMPLES

Example 1. Preparation of "Dimer" Opioid Antagonist Conjugates

Dichlorodimethylsilane or dimethylsilanediyl bis(trifluoromethanesulfonate) (2.5 mmol) is slowly added to a solution of opioid antagonist, for example, naltrexone (5 mmol) in 50 ml of tetrahydrofuran. After 3 hours stirring at room temperature, the resulting suspension is filtered and concentrated. Silica gel chromatography, using ethyl acetate/hexane as the eluent, produces the naltrexone dimer.

Example 2. Preparation of Polymeric Opioid Antagonist Conjugates

Polymeric conjugates of opioid antagonists, for example, naltrexone and naloxone, may be prepared according to Scheme 1 below. For example, polyvinyl acetate is partially deacetylated to provide hydroxyl groups on the polyvinyl acetate chain. Separately, the dichlorodialkylsilyl group (or, e.g., dimethylsilanediyl bis(trifluoromethanesulfonate)ylsilyl group) is attached onto the naloxone or naltrexone or a combination of the two antagonists. The final step involves attaching the silyl/antagonist molecule to the hydroxyl groups of the deacetylated polyvinyl acetate. Depending on the attachments to the silicon group (methyl, ethyl, isopropyl), the rate of release of the antagonist can be modulated.

Scheme 1

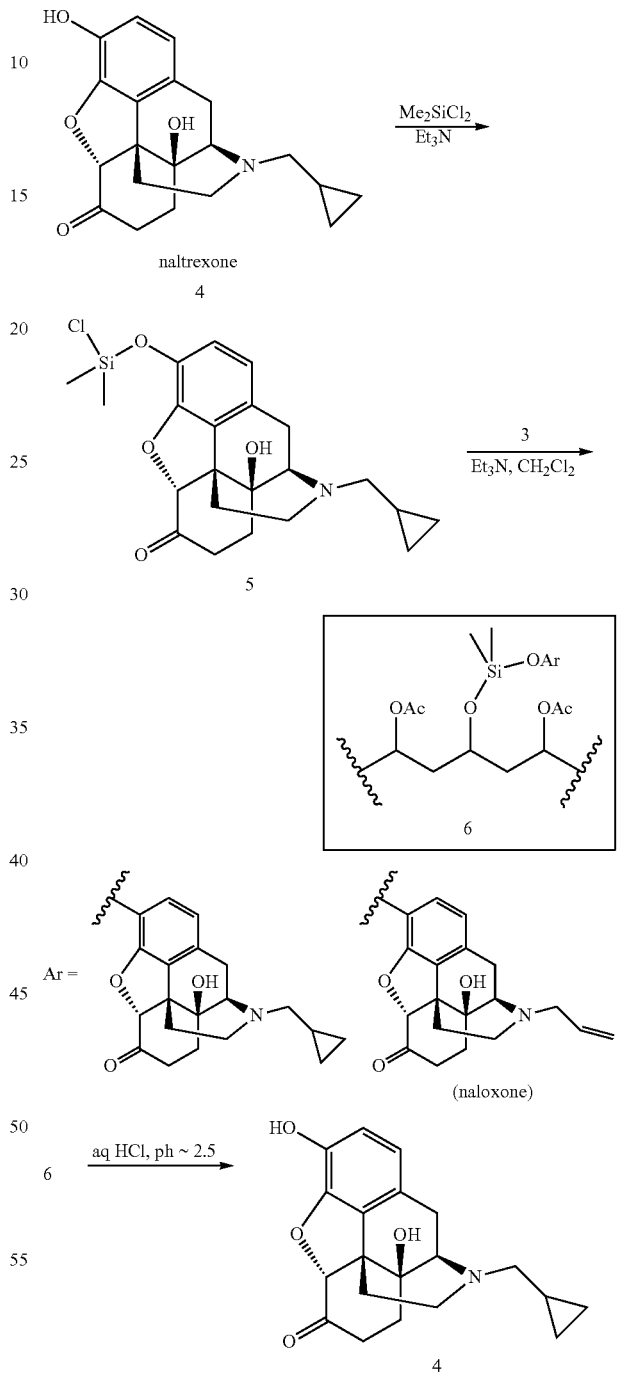

-continued

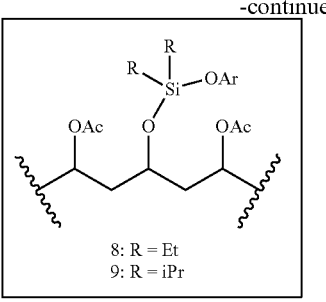

8: R = Et
9: R = iPr

Example 3. Drug in Adhesive Transdermal Patch Preparation

Acrylic/vinyl acetate pressure sensitive adhesive Durotak 87-4098 (PSA) (43% solids) is mixed under continuous stirring with the humectant polyvinyl pyrrolidone/vinyl acetate copolymer (PVP/VA), the enhancers levulinic acid (LVA) and oleic acid (OA), the alkalinizing agent sodium carbonate, the opioid drug oxymorphone, and the naltrexone conjugate of Example 1. The PSA adhesive solution is coated onto the backing Scotchpak 9733 and dried in an oven at 90° C. for 10 minutes, at which time the release liner Scotchpak 9742 is applied on the exposed PSA side. A Warner Mathis Lab Coater, Drying Oven Model (Model LTF, S/N 124188, Coater Model LTSV, S/N 75288) may be used. The thickness of the dried patches (active adhesive portion) is 5 mm and contains 55% Durotak 87-4098, 5% PVP/VA, 5% LVA, 5% OA, 10% oxymorphone and 20% of the naltrexone "dimer" conjugate of Example 1. Skin flux studies through human skin are performed using Franz diffusion cells in triplicate for each patch, with phosphate buffered saline pH 7.4 as the receptor medium. Samples from the receptor phase are obtained at the time intervals of 2, 4, 8, 12, 24, 30, and 48 hours and the oxymorphone and naltrexone that permeated through the skin may be quantified using HPLC.

Example 4. Drug in Adhesive Transdermal Patch with Adhesive Overlay

A transdermal formulation may be prepared as in Example 3, except the opioid agonist is buprenorphine and the opioid antagonist conjugate is the conjugate shown in Example 1 or 2. The thickness of the patch is 10 mm thick so as to contain higher amounts of buprenorphine because the patch is designed to last for 7 days. To provide continuous adhesion for the 7 day period, an overlay of PIB pressure sensitive adhesive is attached on the back of the buprenorphine patch and extending 0.8 cm beyond the active patch in all directions. The pressure sensitive adhesive in the overlay may be a polyisobutylene adhesive (PIB) comprising 50% low molecular weight PIB, 10% high molecular weight PIB and 40% polybutene plasticizer of 3000 centipoise viscosity.

Example 5. Drug in Adhesive Patches Containing Several Opioid Antagonist Conjugates A transdermal formulation may be prepared as in Example 3, except that three opioid antagonist conjugates are incorporated in the patch, for example, the conjugates are those shown in Structures 2 and 3. The use of more than one conjugate renders the opioid in the patch less amenable to abuse.

What is claimed:
1. A transdermal composition comprising
an opioid agonist,
at least one opioid antagonist conjugate that is

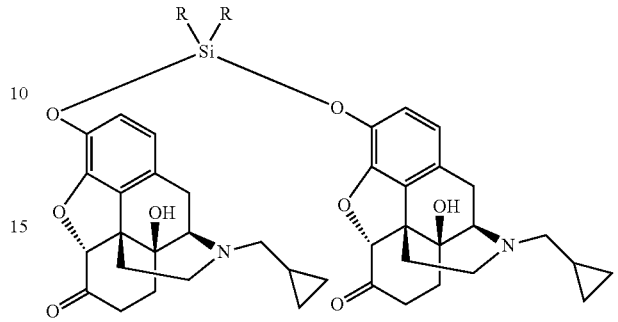

Compound 1, wherein each R is independently $C_{1-6}$ alkyl;

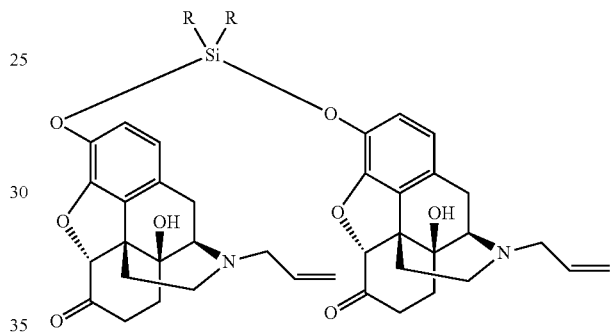

Compound 2, wherein each R is independently $C_{1-6}$ alkyl;

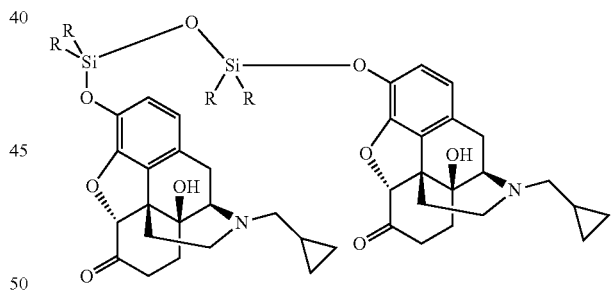

Compound 3, wherein each R is independently $C_{1-6}$ alkyl;

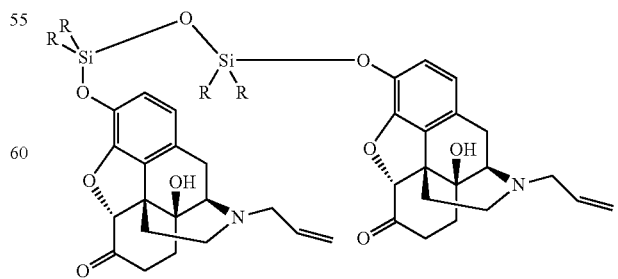

Compound 4, wherein each R is independently $C_{1-6}$ alkyl;

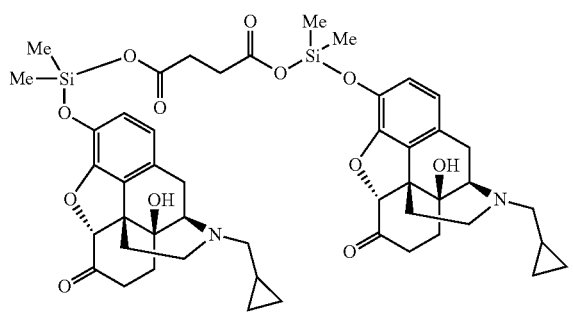 [SMILES: C[Si](C)(OC(=O)CCC(=O)O[Si](C)(C)Oc1ccc2c3c1O[C@H]1C(=O)CC[C@@]4(O)[C@@H](C2)N(CC2CC2)CC[C@]314)Oc1ccc2c3c1O[C@H]1C(=O)CC[C@@]4(O)[C@@H](C2)N(CC2CC2)CC[C@]314]

Compound 5, wherein each R is independently $C_{1-6}$ alkyl;

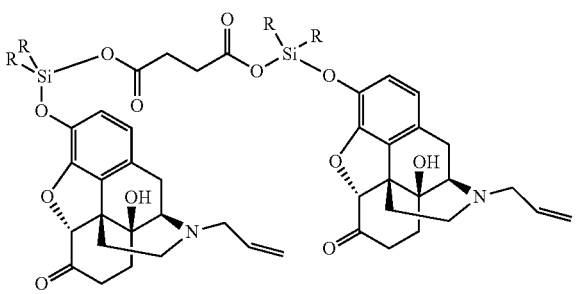

Compound 6, wherein each R is independently $C_{1-6}$ alkyl;

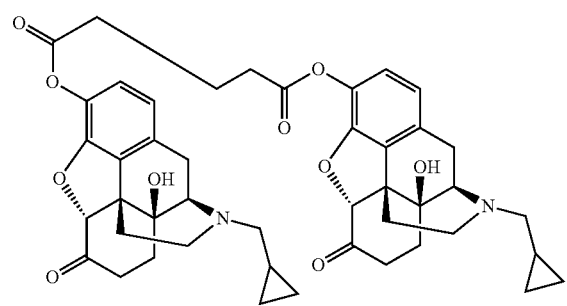 [SMILES: O=C(CCCC(=O)Oc1ccc2c3c1O[C@H]1C(=O)CC[C@@]4(O)[C@@H](C2)N(CC2CC2)CC[C@]314)Oc1ccc2c3c1O[C@H]1C(=O)CC[C@@]4(O)[C@@H](C2)N(CC2CC2)CC[C@]314]

Compound 7, wherein each R is independently $C_{1-6}$ alkyl;

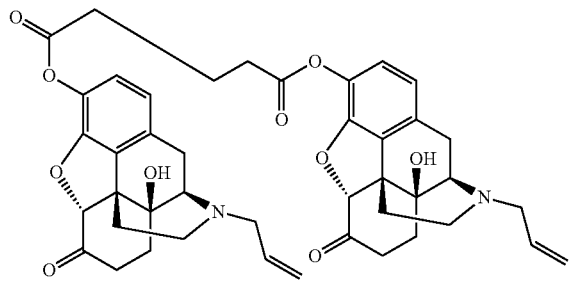 [SMILES: C=CCN1CC[C@]23c4c5ccc(OC(=O)CCCC(=O)Oc6ccc7c8c6O[C@H]6C(=O)CC[C@@]9(O)[C@@H](C7)N(CC=C)CC[C@]869)c4O[C@H]2C(=O)CC[C@@]3(O)[C@H]1C5]

Compound 8, wherein each R is independently $C_{1-6}$ alkyl; or a polymeric conjugate wherein the polymer is attached to a Structure 9:

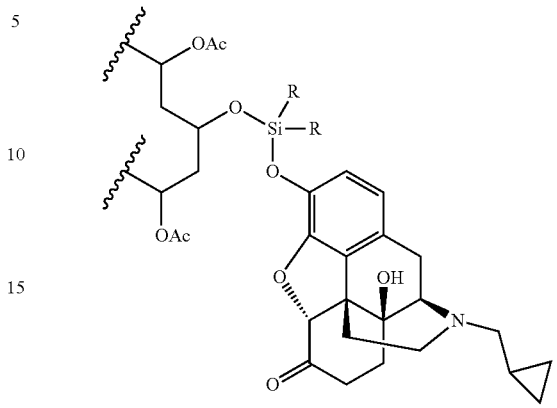

Structure 9, wherein each R is independently $C_{1-6}$ alkyl; or a combination thereof;

and optionally, a pressure-sensitive adhesive, a transdermal skin enhancer, a plasticizer, a humectant, an antioxidant, or a combination thereof.

2. The transdermal composition of claim 1, wherein the opioid agonist is codeine, dihydrocodeine, hydrocodone, hydromorphone, levorphanol, meperidine, fentanyl, dipipanone, heroin, tramadol, etorphine, dihydroetorphmethadone, morphine, oxycodone, oxymorphone, propoxyphene, sufentanil, or buprenorphine, or a pharmaceutically acceptable salt thereof, or a combination thereof.

3. The transdermal composition of claim 1, comprising about 0.1 wt. % to about 40 wt. % of the opioid agonist, by weight of the transdermal composition.

4. The transdermal composition of claim 1, comprising about 0.1 wt. % to about 40 wt. % of the at least one opioid antagonist conjugate, by weight of the transdermal composition.

5. The transdermal composition of claim 1, wherein the opioid antagonist conjugate degrades to produce the opioid antagonist at a pH of between 2 and 4.

6. The transdermal composition of claim 1, wherein the opioid antagonist conjugate degrades to produce the opioid antagonist at a pH of between 6 and 8.

7. The transdermal composition of claim 1, wherein the transdermal skin enhancer comprises levulinic acid and a straight chain fatty acid with one or more double bonds.

8. The transdermal composition of claim 1, wherein the plasticizer is glycerol, polybutylene, or a combination thereof.

9. The transdermal composition of claim 1, wherein the humectant is polyvinyl pyrrolidone or polyvinyl pyrrolidone vinyl acetate copolymer, or a combination thereof.

10. The transdermal composition of claim 1, wherein the antioxidant is butylated hydroxytoluene, butylated hydroxyanisole, propyl gallate, sodium metabisulfite, or tocopherol, or a combination thereof.

11. The transdermal composition of claim 1, wherein the composition is in the form of a device that is a drug-in-adhesive device.

12. The transdermal composition of claim 11, wherein the adhesive is a pressure-sensitive adhesive.

13. The transdermal composition of claim 12, wherein the pressure-sensitive adhesive comprises silicone, a polyisobutylene polymer, or an acrylate copolymer, or a combination thereof.

14. The transdermal composition of claim 1, wherein the composition is in the form of a gel.

* * * * *